United States Patent

Horikiri et al.

[11] Patent Number: 6,054,411
[45] Date of Patent: Apr. 25, 2000

[54] CYANAMIDE AQUEOUS SOLUTION

[75] Inventors: Hitoshi Horikiri, Toyama-ken; Hidenori Nitta, Kanagawa-ken; Masahiro Murotani, Toyama-ken; Hiroaki Obata, Toyama-ken; Kenichi Ishii, Toyama-ken; Atsushi Hirota, Toyama-ken, all of Japan

[73] Assignee: Nippon Carbide Kogyo Kabushiki Kaisha, Tokyo, Japan

[21] Appl. No.: 09/352,118

[22] Filed: Jul. 13, 1999

[30] Foreign Application Priority Data

Jan. 28, 1999 [JP] Japan .................................. 11-019510

[51] Int. Cl.[7] .......................... A01N 37/34; A01N 37/00; A01N 41/12
[52] U.S. Cl. ........................... 504/141; 504/320; 514/609
[58] Field of Search ..................................... 504/116, 141, 504/320, 609

[56] References Cited

U.S. PATENT DOCUMENTS

| | | | |
|---|---|---|---|
| 4,126,664 | 11/1978 | Weiss | 423/265 |
| 4,410,652 | 10/1983 | Robinson et al. | 524/195 |
| 4,883,615 | 11/1989 | Robinson et al. | 428/423.1 |

*Primary Examiner*—Jose' G. Dees
*Assistant Examiner*—Alton Pryor
*Attorney, Agent, or Firm*—Young & Thompson

[57] ABSTRACT

Addition of a dicarboxylic acid such as adipic acid to a cyanamide aqueous solution brings about improvement in storage stability of the cyanamide aqueous solution.

2 Claims, No Drawings

CYANAMIDE AQUEOUS SOLUTION

BACKGROUND OF THE INVENTION

1. [Field of the Invention]

This invention relates to a cyanamide aqueous solution having excellent storage stability.

2. [Description of Related Art]

A cyanamide aqueous solution has been steadily extending its use as a raw material of pharmaceuticals and agricultural chemicals, an antimicrobial agent, a plant protecting agent, an agricultural or horticultural chemical, and the like. Accordingly, there has been a demand for a cyanamide aqueous solution with improved storage stability.

It is known that a cyanamide aqueous solution can be stabilized by adjusting to a pH of 4 to 6. However, this method is disadvantageous in that a sufficient stabilizing effect cannot be obtained unless the solution is kept at about 10 to 20° C. and that the effect does not last long. Addition of 0.03 to 1% by weight of a formic ester has been proposed (see Japanese Patent Publication No. 12206/83), which was also insufficient for securing long-term stability.

SUMMARY OF THE INVENTION

An object of the present invention is to provide a cyanamide aqueous solution having improved storage stability.

The present invention provides a cyanamide aqueous solution containing a compound represented by formula (I), wherein said compound is present in an amount of 0.05 to 1.0% by weight based on the cyanamide aqueous solution exclusive of said compound.

$$HOOC(CH_2)_nCOOH \quad (I)$$

wherein n represents an integer of 0 to 5.

DETAILED DESCRIPTION OF THE INVENTION

The cyanamide aqueous solution which can be used in the present invention is prepared by, for example, starting with lime nitrogen, urea, etc. It is prepared by bubbling carbon dioxide gas through an aqueous solution of the starting material to precipitate calcium carbonate and removing the precipitate by filtration.

The cyanamide aqueous solution is not particularly limited in concentration. A cyanamide aqueous solution as prepared generally has a concentration of from about 20 to 80% by weight.

The dicarboxylic acid represented by formula (I), which is used as a stabilizer for a cyanamide aqueous solution, includes oxalic acid, malonic acid, succinic acid, glutaric acid, adipic acid, and pimelic acid. Of all, adipic acid is particularly preferred.

The amount of the dicarboxylic acid of formula (I) to be added ranges from 0.05 to 1.0 part by weight, preferably from 0.1 to 1.0 part by weight, still preferably from 0.1 to 0.5 part by weight, per 100 parts by weight of the cyanamide aqueous solution.

Where it is less than 0.05 part by weight, the storage stability tends to be insufficient. Addition of more than 1.0 part by weight also results in insufficient storage stability.

The dicarboxylic acid is usually incorporated into the cyanamide aqueous solution by mixing them with stirring. Where lime nitrogen is used as a starting material for the cyanamide aqueous solution, the dicarboxylic acid can be added to the preparation system in any stage of the preparation.

The storage stability of the dicarboxylic acid-containing cyanamide aqueous solution can further be enhanced by adjusting to a pH of 3 to 6, preferably 3 to 5. Suitable pH adjustors include inorganic acids, such as mineral acids, and organic acids, such as acetic acid.

The present invention will now be illustrated in greater detail with reference to Examples in view of Comparative Examples. Unless otherwise noted, all the percents are given by weight.

EXAMPLES 1 AND 2 AND COMPARATIVE EXAMPLES 1 TO 3

In a 300 ml beaker was put 150 g of a cyanamide aqueous solution having a concentration of about 50%, and a pH electrode was immersed therein. While stirring the aqueous solution with a magnetic stirrer, adipic acid was slowly added thereto in an amount of 0.1% (Example 1), 0.5% (Example 2), 0.01% (Comparative Example 2) or 2.0% (Comparative Example 3). In Comparative Example 1, adipic acid was not added. After completion of the addition, the pH of the aqueous solution was adjusted to about 4 with 10% phosphoric acid, followed by filtration through filter paper. A 100 g portion of the filtrate was put in a 100 ml sample bottle, closed with a stopper, and placed in a thermometer kept at 40° C. After 30 days, the cyanamide concentration was measured. The results obtained are shown in Table 1 below.

TABLE 1

| | Stabilizer | | Cyanamide Concn. (Storage Stability) (%) | | Cyanamide |
|---|---|---|---|---|---|
| | Kind | Amount (wt %) | Immediately after Prepn. | After 30 Days | Retention (%) |
| Example 1 | adipic acid | 0.1 | 53.1 | 42.2 | 79.5 |
| Example 2 | adipic acid | 0.5 | 53.0 | 45.8 | 86.4 |
| Compara. Example 1 | none | 0 | 52.9 | 39.0 | 73.7 |
| Compara. Example 2 | adipic acid | 0.01 | 52.9 | 39.0 | 73.7 |
| Compara. Example 3 | adipic acid | 2.0 | 51.3 | 36.2 | 70.6 |

What is claimed is:

1. A cyanamide aqueous solution containing adipic acid in an amount of 0.05 to 1.0% by weight based on the cyanamide aqueous solution exclusive of said adipic acid.

2. The cyanamide aqueous solution according to claim 1, which has a pH of 3 to 6.

* * * * *